US012690794B2

(12) United States Patent (10) Patent No.: US 12,690,794 B2
Nishizawa et al. (45) Date of Patent: Jul. 28, 2026

(54) PROBE, PACKAGED PROBE, EXTERNAL DEVICE COUPLER, AND BIOFEEDBACK DEVICE

(71) Applicants:SOFKEN CO., LTD., Shiroi (JP); NATIONAL CANCER CENTER, Tokyo (JP)

(72) Inventors: Yuji Nishizawa, Tokyo (JP); Takeo Komamura, Shiroi (JP); Kenzo Komamura, Shiroi (JP)

(73) Assignees: SOFKEN CO., LTD., Shiroi (JP); NATIONAL CANCER CENTER, Tokyo (JP)

( * ) Notice: Subject to any disclaimer, the term of this patent is extended or adjusted under 35 U.S.C. 154(b) by 1196 days.

(21) Appl. No.: 17/615,811

(22) PCT Filed: Apr. 3, 2020

(86) PCT No.: PCT/JP2020/015347
§ 371 (c)(1),
(2) Date: Dec. 1, 2021

(87) PCT Pub. No.: WO2021/199434
PCT Pub. Date: Oct. 7, 2021

(65) Prior Publication Data
US 2022/0322990 A1 Oct. 13, 2022

(51) Int. Cl.
*A61B 5/296* (2021.01)
*A61B 5/00* (2006.01)
(Continued)

(52) U.S. Cl.
CPC .............. *A61B 5/296* (2021.01); *A61B 5/25* (2021.01); *A61B 5/389* (2021.01); *A61B 5/6847* (2013.01);
(Continued)

(58) Field of Classification Search
None
See application file for complete search history.

(56) References Cited

U.S. PATENT DOCUMENTS 4,909,263 A * 3/1990 Norris .................. A61N 1/0512
607/39
5,452,719 A 9/1995 Eisman et al.
(Continued)

FOREIGN PATENT DOCUMENTS

CN 109011143 A 12/2018
FR 2 762 983 A1 11/1998
(Continued)

OTHER PUBLICATIONS

Dec. 6, 2022 Search Report issued in European Patent Application No. 20928536.0.
(Continued)

*Primary Examiner* — Jacqueline Cheng
*Assistant Examiner* — Jairo H Portillo
(74) *Attorney, Agent, or Firm* — Oliff PLC

(57) ABSTRACT

A probe includes an insertion portion insertable into a body organ, a projecting portion being exposed to an outside of a body after the insertion portion is inserted into the body organ, a device mounting area onto which an external-device coupler is removably mountable, and sensing electrodes provided on the insertion portion and the device mounting area. When the insertion portion is inserted into the body organ, the sensing electrodes detect a biosignal and become conductive with coupling electrodes of the external-device coupler mounted onto the device mounting area. The probe is an electromyograph probe that detects a biosignal measurable by an electromyograph. The insertion portion and the projecting portion of the probe may be integrated or separate from each other. Both of the insertion portion and (Continued)

the projecting portion or only the insertion portion may be disposable.

12 Claims, 15 Drawing Sheets

(51) Int. Cl.
  *A61B 5/25* (2021.01)
  *A61B 5/389* (2021.01)
(52) U.S. Cl.
  CPC ........ *A61B 5/742* (2013.01); *A61B 2562/225* (2013.01)

(56) References Cited

U.S. PATENT DOCUMENTS

| | | | | |
|---|---|---|---|---|
| 5,881,731 A | * | 3/1999 | Remes | A61N 1/0512 128/885 |
| 2007/0239224 A1 | * | 10/2007 | Bennett | A61N 1/36007 607/41 |
| 2009/0222058 A1 | * | 9/2009 | Craggs | A61N 1/0512 607/138 |
| 2009/0270963 A1 | * | 10/2009 | Pelger | A61N 1/0524 600/372 |
| 2018/0296383 A1 | * | 10/2018 | Blanche | A61H 19/44 |

FOREIGN PATENT DOCUMENTS

| | | | |
|---|---|---|---|
| JP | S63-29618 | A | 2/1988 |
| JP | 2003-180840 | A | 7/2003 |
| JP | 2009-538176 | A | 11/2009 |
| JP | 2020-75122 | A | 5/2020 |
| JP | 6813232 | B1 | 1/2021 |
| WO | 2007/136266 | A1 | 11/2007 |
| WO | 2011/051775 | A2 | 5/2011 |
| WO | 2017/070746 | A1 | 5/2017 |
| WO | 2019/200222 | A1 | 10/2019 |

OTHER PUBLICATIONS

Feb. 17, 2023 Search Report issued in Indian Patent Application No. 202227053463.

Aug. 1, 2023 Office Action issued in Japanese Patent Application No. 2019-199791.

Aug. 15, 2023 Examination Report issued in Canadian Patent Application No. 3,164,172.

EMG Electrode, Stimulation/Vaginal/Reusable, T6050, Thought Technology, (2020), pp. 1-5, url: http://www.medicalexpo.com/ja/prod/thought-technology/product-70321-739531.html.

Rectal Sensor til U-Controlbekkenbunnopptrener, BioStim AS, (2020), pp. 1-2, url: https://www.biostim.no/produkt/rektal-sensor-u-control-bekkenbunnopptrener/.

Vaginal Pelvic Muscle Probe, Perisphera®e, Beacmed, (2020), pp. 1-4, url: http://www.medicalexpo.it/prod/beacmed/product-67740-600829.html.

Vaginal Probe in Case of Incontinence. Pelvic Floor Muscles, EMS-Vaginalsonde gegen Inkontinenz, Beckenbodentrainer mit elektrischer Muskelstimulation (EMS), (2020), pp. 1-3, url: https://beckenboden-trainer.de/sonden/vaginalsonden/32/vaginalsonde-bei-inkontinenz.-beckenbodenmuskulatur.

EMG Stim EMS & Bio-Feedback EMG Full Pelvic Floor Exercise for Super Slim Vagina or Probe, (2021), pp. 1-6, url: https://ja.aliexpress.com/store/product/Super-Slim-Vaginal-or-Anal-Probe-for-EMG-STIM-EMS-Biofeedback-EMG-TENS-PELVIC-FLOOR-EXERCISERS/234181_32414048195.html.

Pathway Rectal Sensor for EMG Units and E-Stimulators, Adavantage Medical, (2020), pp. 1-2, url: https://www.advantagemedical.com/products/pathway-rectal-sensor-for-emg-and-e-stim/.

Rectal Sensor with Stim, MedQuip, Inc., (2020), pp. 1, url: https://medicalquip.com/product/rectal-sensor-with-stim/.

Design U.S. Appl. No. 29/751,501, filed Sep. 22, 2020 in the name of Takeo Komamura et al.

Sep. 15, 2020 Office Action issued in Japanese Patent Application No. 2020-535664.

Jun. 23, 2020 Search Report issued in International Patent Application No. PCT/JP2020/015347.

Jun. 23, 2020 Written Opinion issued in International Patent Application No. PCT/JP2020/015347.

Feb. 20, 2024 Office Action issued in Indonesian Patent Application No. P00202208158.

Jun. 3, 2024 Office Action issued in Indonesian Patent Application No. P00202208158.

* cited by examiner

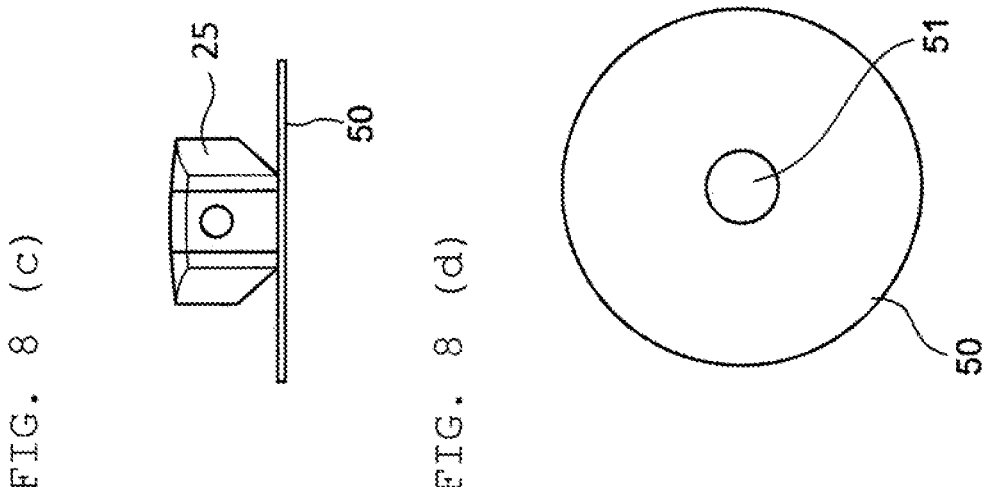
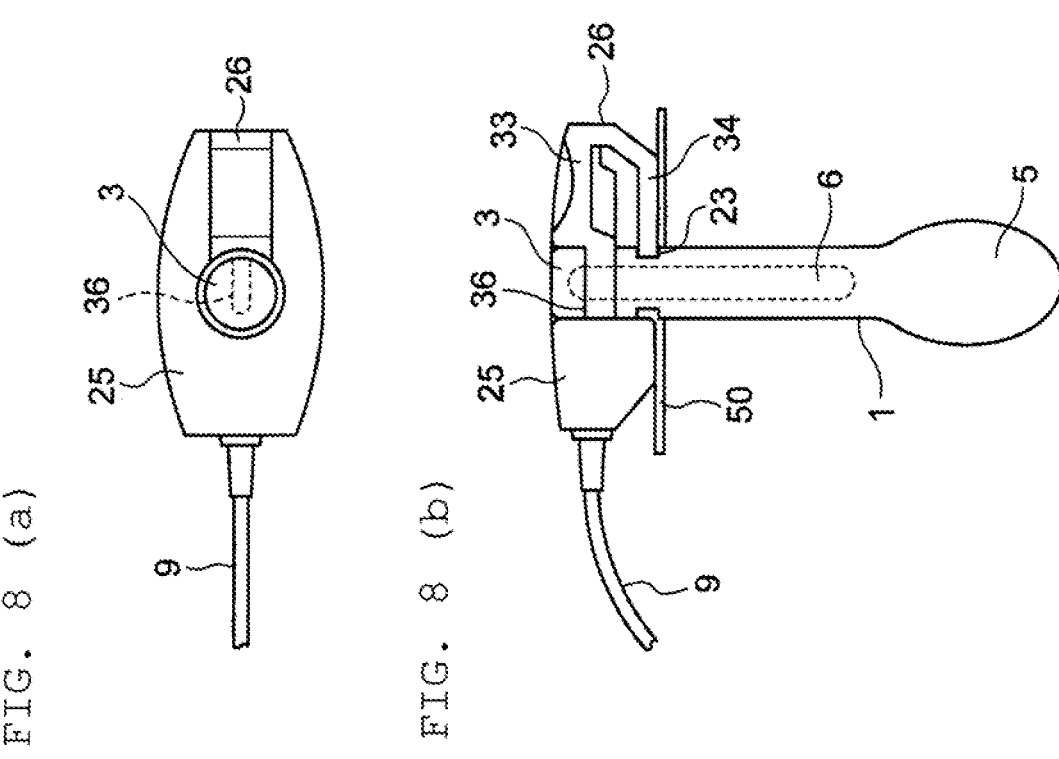

PROBE, PACKAGED PROBE, EXTERNAL DEVICE COUPLER, AND BIOFEEDBACK DEVICE

TECHNICAL FIELD

The present invention relates to a probe that is to be inserted into an anus, a woman's vagina, or other measurement site and used for measurement of an action potential (myopotential) of pelvic floor muscles (an external anal sphincter and an internal anal sphincter), a package probe including the probe contained in a package, an external-device coupler that enables coupling of an external device (for example, an electromyograph) to the probe, and a biofeedback device that generates perceivable information based on a biosignal detected by the probe.

BACKGROUND ART

An electromyograph is a device (measurement device) that detects a biosignal (body signal) resulting from a muscle activity of, for example, an external anal sphincter or pelvic floor muscles to measure a muscle strength, a change in muscle strength, or the like (perform muscle strength measurement) of the external anal sphincter or the pelvic floor muscles so as to strengthen the muscle or treat and prevent urine leakage or incontinence while checking the measured biosignal. An electromyograph probe, which is inserted into a measurement site (hereinafter referred to as "body organ") such as an anus or a vagina, is used to detect a biosignal. Electromyograph probes (hereinafter referred to as "probes") are commercially available, and have various shapes (Non Patent Literatures 1 to 7).

A representative one of probes described in Non Patent Literatures 1 to 7 mainly includes, as illustrated in FIG. 15, an insertion portion A to be inserted into a body organ, and two electrodes C. The electrodes C are provided on an outer peripheral surface of a shaft B of the insertion portion A so as to be opposed to each other. When the insertion portion A is inserted into a body organ in such a manner that the entire shaft B is fully placed inside the body organ, both the electrodes C are brought into contact with, for example, the external anal sphincter or the pelvic floor muscles to detect a biosignal from the muscles described above. The biosignal detected by the two electrodes C is transmitted to a signal processing unit D of an electromyograph, and a potential difference from reference electrodes attached at suitable positions on a surface of the body is measured.

The probe is inserted into a body organ. Thus, from a hygienic viewpoint, the probe is generally discarded after each use. However, when each probe is discarded after single use, cost increases for the following reasons. Each probe is as expensive as several thousand Japanese yen. In addition, as illustrated in FIG. 15, a lead wire (cable) E led out from the signal processing unit D of the electromyograph is directly attached (fixed) inside a handle F of the probe. Further, each of the insertion portion A, the electrodes C, and the lead wire E has a mechanical strength that allows repeated use. Thus, it is regrettable to discard the above-mentioned components after single use. Under current conditions, the probe is disinfected or sterilized after each use for subsequent use. However, such use of the probe may lead to hygienic problems, and users may be reluctant to use the probe in the above-mentioned manner.

CITATION LIST

Non Patent Literature

[NPL  1]  http://www.medicalexpo.com/ja/prod/thought-technology/product-70321-739531.html
[NPL  2]  https://www.biostim.no/produkt/rektal-sensor-u-control-bekkenbunnopptrener/
[NPL 3] http://www.medicalexpo.it/prod/beacmed/product-67740-600829.html
[NPL 4] https://beckenboden-trainer.de/sonden/vaginalson-den/32/vaginalsonde-bei-inkontinenz.-beckenboden-muskulatur
[NPL 5] https://ja.aliexpress.com/store/product/Super-Slim-Vaginal-or-Anal-Probe-for-EMG-STIM-EMS-Biofeed-back-EMG-TENS-PELVIC-FLOOR-EXERCISERS/234181_32414048195.html
[NPL 6] https://www.advantagemedical.com/products/path-way-rectal-sensor-for-emg-and-e-stim/
[NPL  7]  https://medicalquip.com/product/rectal-sensor-with-stim/

SUMMARY OF INVENTION

Technical Problem

An object of the present invention is to provide a probe that is easy to use and hygienic, a packaged probe that is usable hygienically, an external-device coupler that enables easy coupling of an external device to the probe, and a biofeedback device that perceptualizes a biosignal detected by the probe.

Solution to Problem

[Probe]

According to the present invention, there is provided a probe including an insertion portion insertable into a body organ and a projecting portion that is exposed to an outside of a body after the insertion portion is inserted into the body organ. The projecting portion has a device mounting area. Electrodes (hereinafter referred to as "sensing electrodes") that detect a biosignal when the insertion portion is inserted into the body organ are provided on the insertion portion and the device mounting area. When an external-device coupler is mounted onto the device mounting area, the biosignal detected by the sensing electrodes is transmitted to an external device.

[Packaged Probe]

According to the present invention, there is provided a packaged probe including a package that contains the probe. A part of the package can be cut away to open the package. When the package is opened, the insertion portion or the projecting portion of the probe is exposed from an opening and another one of the insertion portion and the projecting portion remains in the package. A separation sheet may be packaged together with the probe. When the separation sheet is placed on an outer periphery of the projecting portion, the separation sheet can prevent contact of a leakage flowing out from the body organ with the projecting portion.

[External-Device Coupler]

According to the present invention, there is provided an external-device coupler including a mounting portion removably mountable to the device mounting area of the probe and electrodes (hereinafter referred to as "coupling electrodes") to be brought into contact with the sensing electrodes of the probe to become conductive with the sensing electrodes when the mounting portion is mounted to the device mounting area.

[Biofeedback Device] According to the present invention, there is provided a biofeedback device that enables use of perceivable information for biofeedback evaluations and treatments. The perceivable information is generated in the external device after the biosignal detected by the sensing electrodes of the probe is transmitted to the external device via the external-device coupler. The perceivable information includes, for example, image information and audio information. When the perceivable information is the image information, an image is displayed on a monitor screen. The image can be viewed and used for biofeedback evaluations and treatments. The perceivable information may be stored in a storage device.

Advantageous Effects of Invention

The probe according to the present invention has the following effects.

1. When the insertion portion is inserted into a body organ, the sensing electrodes detect the biosignal.

2. When the external-device coupler is mounted onto the device mounting area, the biosignal detected by the sensing electrodes can be transmitted to the external device.

3. When a separation sheet is mounted around the projecting portion, the separation sheet stops flow of a leakage from a body organ and prevents the leakage from coming into contact with the projecting portion. Thus, contact of a hand with the leakage is prevented, and thus the probe is hygienic.

When a part of the package of the packaged probe according to the present invention is cut away to open the package, the insertion portion or the projecting portion is exposed to an outside of the package. The insertion portion or the projecting portion, which remains in the package, is held with a hand together with the package, and thus can be inserted into and removed from a body organ without being directly touched by a hand. Thus, the packaged probe is hygienic.

The external-device coupler according to the present invention enables easy mounting of the external device to the device mounting area of the probe. Thus, the biosignal detected by the probe can be reliably transmitted to the external device.

The biofeedback device according to the present invention enables the biosignal detected by the sensing electrodes of the probe to be checked in the form of the perceivable information. Thus, the biofeedback device can be effectively used for biofeedback evaluations and treatments.

BRIEF DESCRIPTION OF DRAWINGS

FIG. 8(a) is a plan view of the external-device coupler of FIG. 5, FIG. 8(b) is an explanatory side view for illustrating a case in which the external-device coupler of FIG. 5 is mounted to the probe, FIG. 8(c) is a front view of the extension arm member of FIG. 5, and FIG. 8(d) is a plan view of the separation sheet.

FIG. 12 is a perspective view for illustrating a state in which the probe illustrated in FIG. 11(a) and FIG. 11(b) is assembled.

BRIEF DESCRIPTION OF DRAWINGS

DESCRIPTION OF EMBODIMENT

First Embodiment of Integrated Probe

Figure 1:
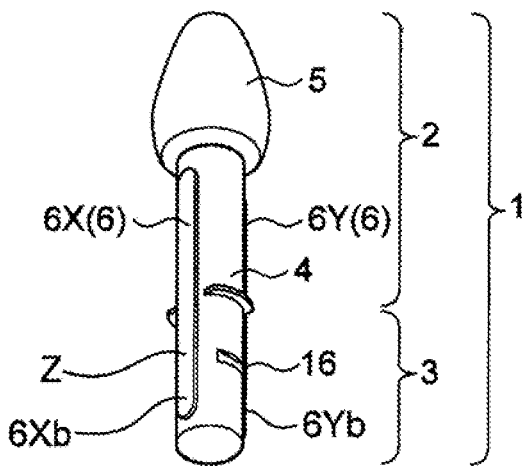
FIG. 1(a) is a perspective view of an example of a probe according to the present invention.
FIG. 1(b) is a perspective view for illustrating a state in which a separation sheet is mounted around an insertion portion of the probe.
Figure 1:
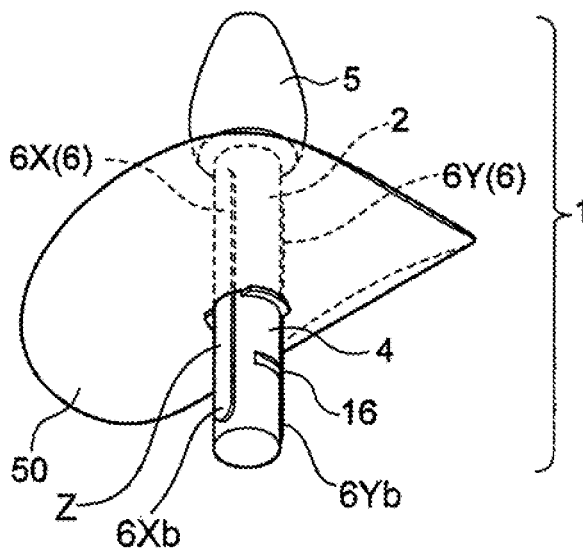

As an example of the present invention, a probe 1 is illustrated in FIG. 1(a). The probe 1 is an integrated probe including an insertion portion 2 and a projecting portion 3 that are continuous with each other. The insertion portion 2 is located on a front end side of one base 4 having a rod-like or cylindrical shape, and the projecting portion 3 is located on a rear end side thereof. A device mounting area Z (FIG. 1 and FIG. 2) is defined on a rear end side of the projecting portion 3.

The insertion portion 2 includes an expanded portion 5 provided on the front end side of the base 4 and part of the base 4, which is located on a side closer to a root of the expanded portion 5. The insertion portion 2 is to be inserted into a body organ. The expanded portion 5 is tapered for easy insertion into a body organ, and is also formed thicker than the projecting portion 3 for prevention of unintended removal from the body organ. A length, a diameter, a shape, and other dimensions of the insertion portion 2 may be suitably designed. The above-mentioned dimensions and shape may be the same as or different from those of existing anal or vaginal probes.

Figure 2:
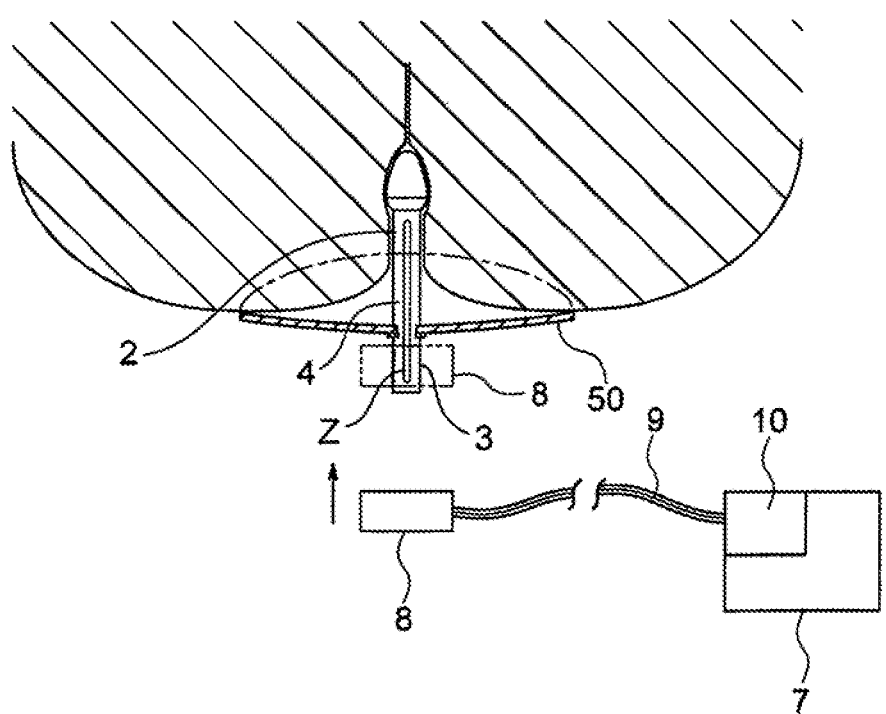
FIG. 2 is an explanatory view for illustrating a state in which the probe according to the present invention is inserted into a body organ and the separation sheet is placed so as to be in contact with buttocks.

The insertion portion 2 can be inserted into a body organ. The projecting portion 3 is designed so that the device mounting area Z is exposed to an outside of a body after the insertion portion 2 is inserted into a body organ (FIG. 2). A length, a diameter, a shape, and other dimensions of the projecting portion 3 may be suitably designed. The above-mentioned dimensions and shape may be the same as or different from those of existing anal or vaginal probes.

[Sensing Electrodes]

Sensing electrodes 6 (FIG. 1(*a*)) are provided on an outer peripheral surface of the insertion portion 2. Two sensing electrodes 6 (6X and 6Y) are provided on an outer peripheral surface of the projecting portion 3 so as to be opposed to each other. The two sensing electrodes 6X and 6Y are each, for example, an electroconductive thin metal plate, metal film, or thin metal film. When the insertion portion 2 is inserted into a body organ, the sensing electrodes 6X and 6Y are brought into contact with a muscle (hereinafter referred to as "body-organ muscle") such as an external anal sphincter or pelvic floor muscles of the body organ to detect a biosignal. When the sensing electrodes 6X and 6Y are thin metal plates or metal films, the sensing electrodes 6X and 6Y can be fixed onto an outer peripheral surface of the base 4. A suitable method may be used as fixing means. When thin films are used as the sensing electrodes 6X and 6Y, the thin films may be formed on the outer peripheral surface of the base 4 by means such as adhesion, spraying, or coating. A length and a width of each of the two sensing electrodes 6X and 6Y are set to allow the insertion portion 2 to be brought into contact with a body-organ muscle when the insertion portion 2 is inserted into a body organ. In FIG. 1 and FIG. 2, the sensing electrodes 6X and 6Y extend from the insertion portion 2 to the device mounting area Z (FIG. 1 and FIG. 2) of the projecting portion 3 so that the extended portions from projecting-portion electrodes 6Xb and 6Yb. When an external-device coupler 8 (FIG. 2) is mounted onto the device mounting area Z (FIG. 1 and FIG. 2), electrodes (coupling electrodes) of the external-device coupler 8 are brought into contact with the projecting-portion electrodes 6Xb and 6Yb so as to be electrically conductive therewith.

First Embodiment of External-Device Coupler

The external-device coupler (hereinafter simply referred to as "coupler") 8 is electrically connected to a signal processing unit 10 of an external device 7 via a lead wire 9 (FIG. 2). In this embodiment, the external device 7 is an electromyograph. However, the electromyograph is merely an example. In the present invention, any other devices that are capable of generating perceivable information (perceivable signal) to be used for biofeedback based on the biosignal detected by the sensing electrodes may be used as the external device 7.

Figure 3:
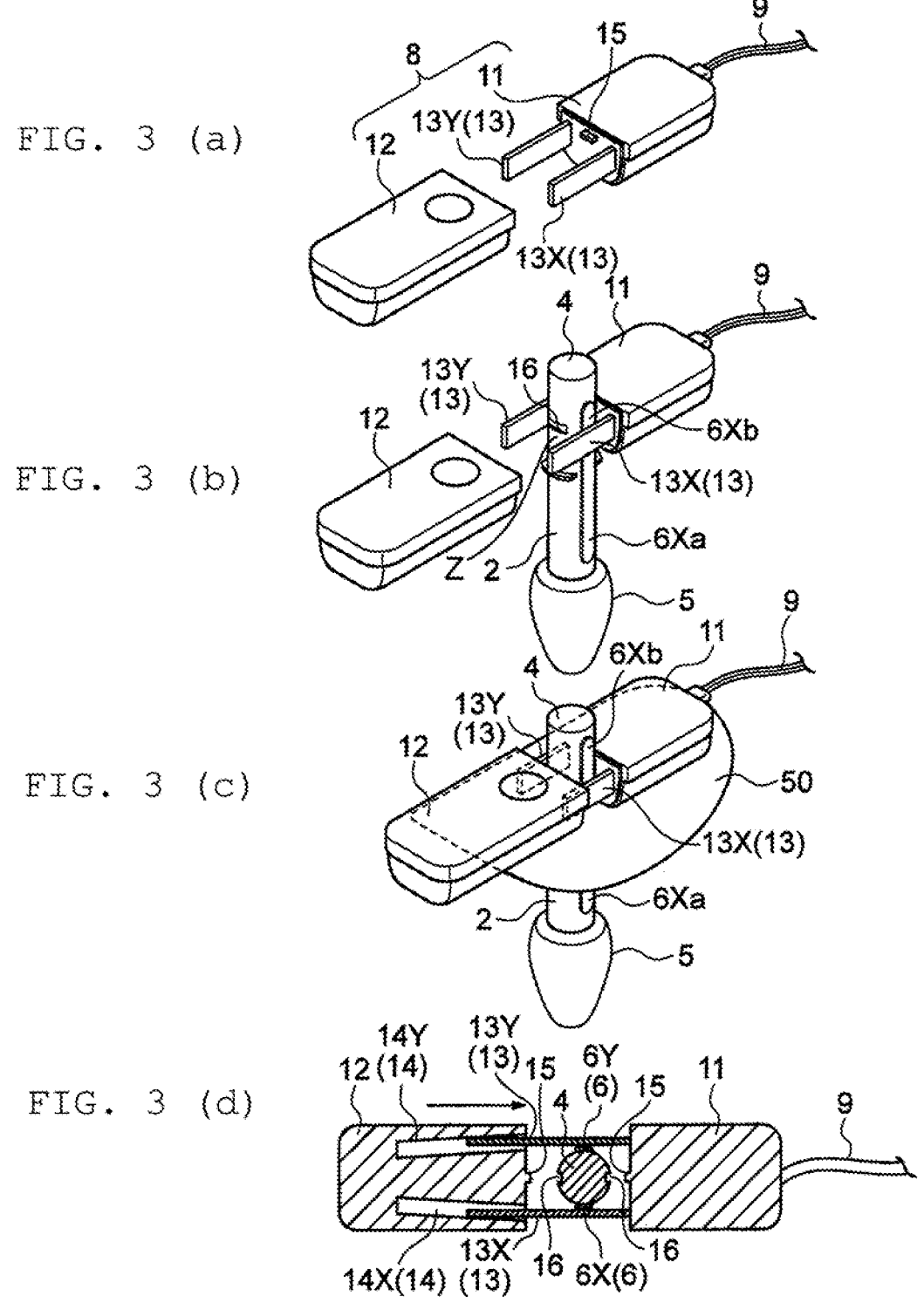
FIG. 3(a), FIG. 3(b), FIG. 3(c), and FIG. 3(d) are explanatory views for illustrating a case in which an electromyograph is coupled to a projecting portion of the probe according to the present invention with an external-device coupler.

Various structures and mechanisms are conceivable for the coupler 8. As an example, the coupler 8 illustrated in FIG. 3(*a*) to FIG. 3(*d*) includes a male coupler member 11 and a female coupler member 12, which can removably mate to each other. The male coupler member 11 includes male electrodes 13 (13X and 13Y). The female coupler member 12 has two insertion holes 14 (14X and 14Y) into which the male electrodes 13X and 13Y are insertable. The two male electrodes 13X and 13Y are parallel in a longitudinal direction. The two insertion holes 14X and 14Y are formed so as to be parallel on an inlet side and become closer to each other in a depth direction. With this structure, when the two male electrodes 13X and 13Y are inserted into the two insertion holes 14X and 14Y, the male electrodes 13X and 13Y are brought closer to each other and brought into pressure-contact with the sensing electrodes 6Xb and 6Yb of the probe 1. As a result, the sensing electrodes 6X and 6Y become conductive with the male electrodes 13X and 13Y of the coupler 8 and the signal processing unit 10 via the lead wire 9, allowing the biosignal detected by the sensing electrodes 6X and 6Y to be transmitted to the signal processing unit 10. Protrusions 15 are formed on inner surfaces of the male coupler member 11 and the female coupler member 12, respectively. When the male coupler member 11 and the female coupler member 12 are brought into abutment against the outer peripheral surface of the projecting portion 3 as illustrated in FIG. 3(*c*), the protrusions 15 are inserted into recessed portions 16 (FIG. 3(*b*) and FIG. 3(*d*)) formed on the outer peripheral surface of the projecting portion 3 to thereby prevent rotation of the male coupler member 11 and the female coupler member 12 about an axis of the projecting portion 3. The signal processing unit 10 is configured to process the biosignal detected by the sensing electrodes 6X and 6Y on the insertion portion 2.

(Second Embodiment of External-Device Coupler)

Figure 4:
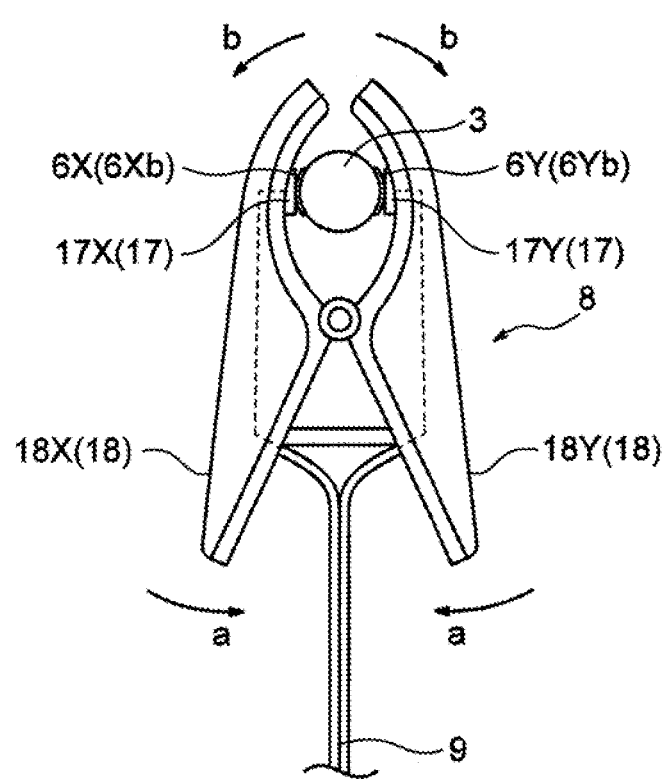
FIG. 4 is an explanatory view for illustrating a case in which the external-device coupler to be coupled to the probe according to the present invention is a clip.

Another example of the coupler 8 is illustrated in FIG. 4. The coupler 8 is a clip. The clip can be opened and closed like a general-purpose clothespin. The coupler 8 includes clamping electrodes 17 (17X and 17Y) provided on inner surfaces at distal ends of the coupler 8, and operating portions 18X and 18Y on a rear side. In FIG. 4, illustration is given of a state in which the two clamping electrodes 17X and 17Y are closed to clamp and hold the sensing electrodes 6Xb and 6Yb of the probe 1. When the two operating portions 18X and 18Y are moved closer to each other in directions indicated by arrows "a", the distal ends are opened in directions indicated by arrows "b" to release the clamping. When the probe 1 is clamped and held, the sensing electrodes 6X and 6Y become electrically conductive with the clamping electrodes 17X and 17Y and the signal processing unit 10 via the lead wire 9. When the clamping is released, the conduction is interrupted.

(Second Embodiment of Integrated Probe)

Figure 5:
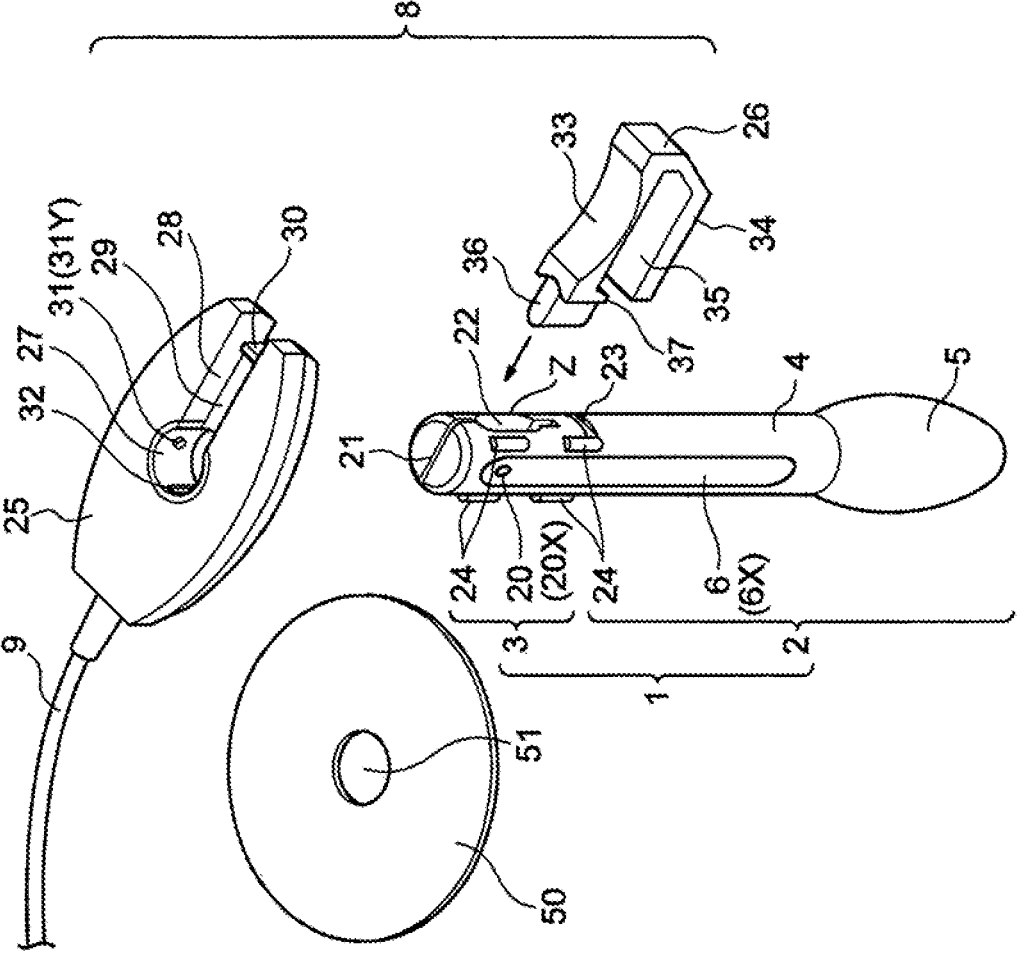
FIG. 5 is an explanatory view of another example of the probe and the external-device coupler according to the present invention.

Another example of the probe 1 according to the present invention, which is illustrated in FIG. 5, is also an integrated probe including the insertion portion 2 and the projecting portion 3 that are continuous with each other. The probe 1 also includes the two sensing electrodes 6X and 6Y that are arranged on the projecting portion 3 so as to be opposed to each other. Two electrode protrusions 20 (20X and 20Y) are formed in a protruding manner on upper parts of the sensing electrodes 6X and 6Y, respectively. One electrode protrusion 20X is illustrated in FIG. 5. However, another electrode protrusion 20Y is located on a back side of the electrode protrusion 20X, and thus is not illustrated in FIG. 5. An end of the base 4 is divided into two parts by a division groove 21, and the two parts can be horizontally opened and closed. An upper groove 22 having a longitudinally elongated shape and a lower groove 23 having a horizontally elongated shape are formed below the division groove 21 to pass through the base 4 in a width direction. Rotation stopping protrusions 24 are formed in a protruding manner on the outer peripheral surface of the base 4 so as to be adjacent to the upper groove 22.

Figure 6:
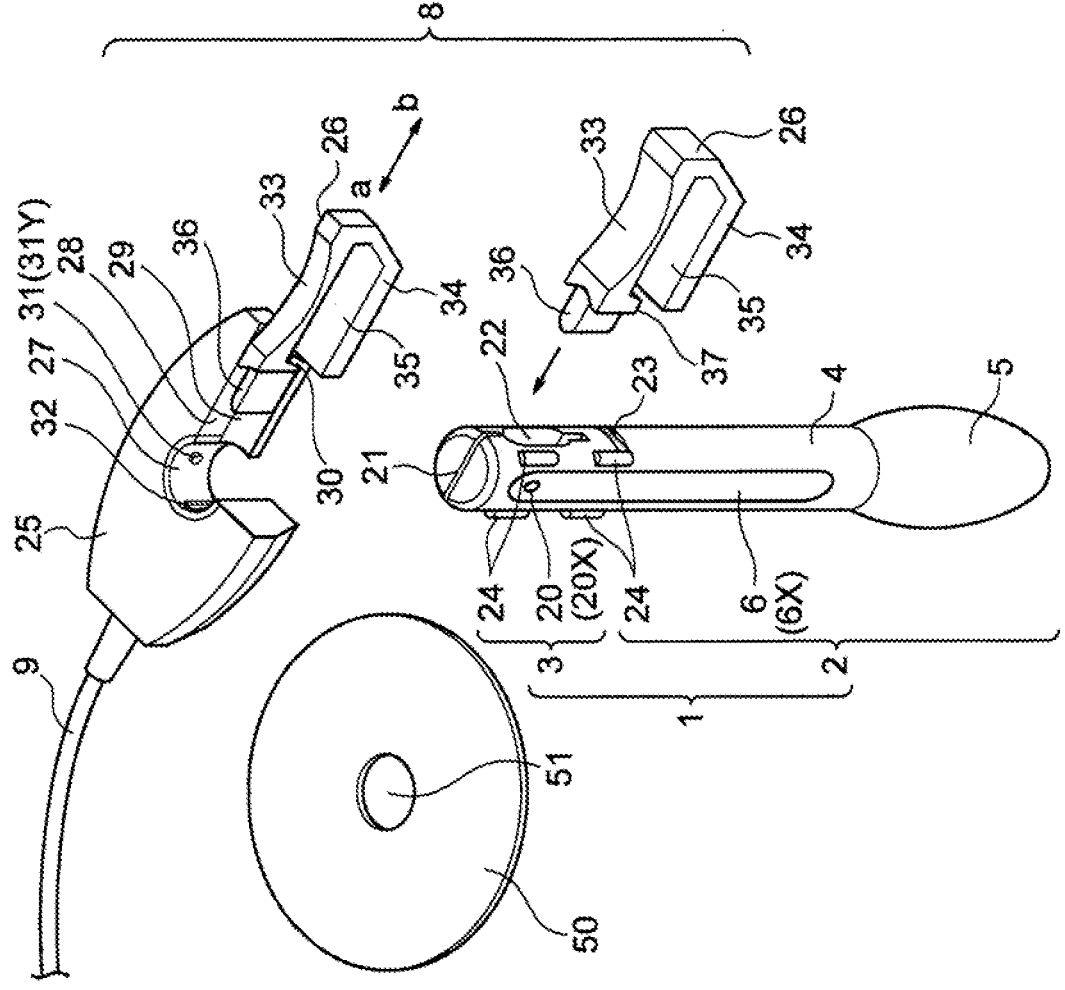
FIG. 6 is an explanatory view for illustrating mounting of the probe and the external-device coupler illustrated in FIG. 5.

The coupler 8 illustrated in FIG. 5, which is to be coupled to the probe 1, includes a coupler main body 25 and an extension arm member 26 as illustrated in FIG. 5 and FIG. 6. The coupler main body 25 has an ellipsoidal plate-like shape with a large thickness, and has a fitting hole 27 and a fitting recessed portion 28. The fitting hole 27 is formed in a center of the coupler main body 25 in a horizontal direction to vertically pass through the coupler main body 25. The fitting recessed portion 28 having a horizontally elongated shape is formed on a distal end side of the coupler main body 25. The fitting recessed portion 28 has an inner side (left side) communicating with the fitting hole 27 and has an open distal end (right end) on an outer peripheral surface of a distal end of the coupler main body 25. The coupler main body 25 has a fitting plate 29 in a center in a thickness direction of the coupler main body 25. A retaining protrusion 30 is formed at a distal end of the fitting plate 29 so as to protrude upward. Two electrode protrusions 31 (31X and 31Y) are formed on an inner peripheral surface of the fitting hole 27 so as to be opposed to each other. The lead wire 9 of the external device is directly connected to the electrode protrusions 31X and 31Y. The lead wire 9 is led out from a rear end of the coupler main body 25. A rotation stopper portion 32 (FIG. 5 and FIG. 6) having a recessed shape is also formed in the inner peripheral surface of the fitting hole 27. The rotation stopper portion 32 may have a protruding shape.

Figure 7:
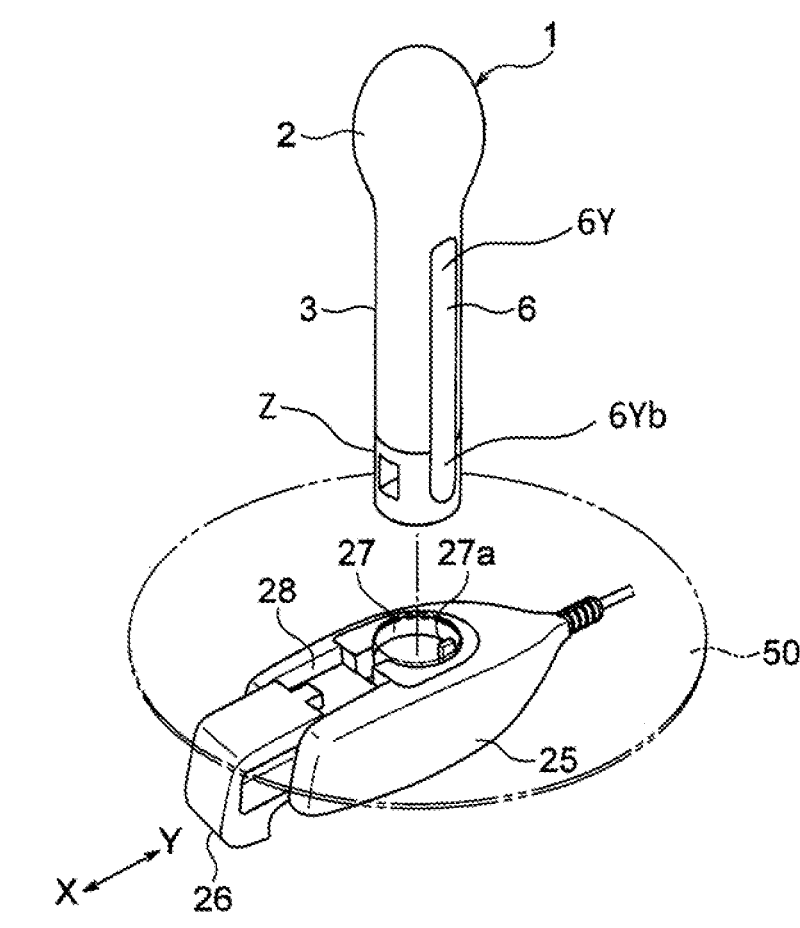
FIG. 7(a) is an explanatory view of the external-device coupler before insertion of an extension arm member.
FIG. 7(b) is an explanatory view of the external-device coupler after the insertion of the extension arm member.

In order to prevent upside-down insertion of the probe 1 into the fitting hole 27, a regulating protrusion 27a may be formed on the inner peripheral surface of the fitting hole 27 so as to be closer to one opening of the fitting hole 27 as illustrated in FIG. 7(a). When the regulating protrusion 27a is formed, the probe 1 can be inserted from a front side or a back side (any one of the sides) of the fitting hole 27. However, the probe 1 cannot be inserted from another one of the sides. This structure prevents insertion of the probe 1 into the fitting hole 27 with an inappropriate orientation. When the probe 1 is inserted with a correct orientation, a distal end of the probe 1 abuts against the regulating protrusion 27a to thereby position the upper groove 22 of the probe 1 at a predetermined position.

The extension arm member 26 illustrated in FIG. 5 includes an upper plate 33, a lower plate 34, and a fitting groove 35 defined between the upper plate 33 and the lower plate 34. The fitting groove 35 has an open left end, and has a horizontally elongated U-like shape in side view. A push-in protrusion 36 protrudes forward from a distal end of the upper plate 33. A stopper 37 protrudes downward from the distal end of the upper plate 33. The extension arm member 26 can reciprocally slide in directions indicated by arrows "a" and "b" in FIG. 6. When the extension arm member 26 is pushed in the direction indicated by the arrow "a", the fitting groove 35 is fitted over the fitting plate 29 of the fitting recessed portion 28. When the extension arm member 26 is pulled in the direction indicated by the arrow "b" as illustrated in FIG. 6, the stopper 37 is caught by the retaining protrusion 30 to retain the extension arm member 26 in the fitting recessed portion 28.

The extension arm member 26 illustrated in FIG. 5 and FIG. 6 is inserted and placed in the coupler main body 25 as illustrated in FIG. 7(a) and FIG. 7(b), and can reciprocally slide in directions indicated by arrows X and Y. In FIG. 7(a), the extension arm member 26 is slid in the direction indicated by the arrow X and is pulled out from the coupler main body 25 to expose the fitting hole 27. In FIG. 7(b), after a separation sheet 50 is placed and the probe 1 is inserted into the fitting hole 27, the extension arm member 26 is pushed into the direction indicated by the arrow Y to fix the probe 1 in the fitting hole 27. Under this fixed state, the sensing electrodes 6X and 6Y of the probe 1 are held in contact with the electrode protrusions 31X and 31Y of the coupler 8 to achieve a conductive state.

(Example of Use of External-device Coupler)

The probe 1 is inserted into the fitting hole 27 of the coupler 8 as illustrated in FIG. 8(a) and FIG. 8(b). The projecting portion 3 of the probe 1 is inserted vertically into the fitting hole 27 of the coupler main body 25. At this time, the rotation stopping protrusion 24 (FIG. 6) formed on the outer peripheral surface of the base 4 of the probe 1 is fitted into the rotation stopper portion 32 (FIG. 5 and FIG. 6) formed in the inner peripheral surface of the fitting hole 27 to thereby prevent spinning of the probe 1. Under this state, the extension arm member 26 is pushed into the fitting recessed portion 28 of the coupler main body 25 to insert the push-in protrusion 36 of the extension arm member 26 into the upper groove 22 (FIG. 6) formed in a peripheral surface of the base 4 of the probe 1 as illustrated in FIG. 8(a). As a result, two separate upper ends of the base 4 are forced apart from each other in the horizontal direction to push the electrode protrusions 20X and 20Y formed on the sensing electrodes 6X and 6Y of the probe 1 against the electrode protrusions 31X and 31Y formed inside the fitting hole 27 to achieve contact therebetween. At this time, as illustrated in FIG. 8(b), the lower plate 34 of the extension arm member 26 is inserted into the lower groove 23 of the base 4 to ensure the contact between the electrode protrusions 20X and 20Y and the electrode protrusions 31X and 31Y formed inside the fitting hole 27 of the coupler 8. This coupling enables the electrode protrusions 20X and 20Y formed on the sensing electrodes 6X and 6Y to become conductive with the coupling electrodes 31X and 31Y formed inside the fitting hole 27 and the signal processing unit 10 via the lead wire 9. As a result, the biosignal detected by the sensing electrodes 6X and 6Y is transmitted to the signal processing unit 10.

(Embodiment of Disassemblable Probe)

Figure 10:
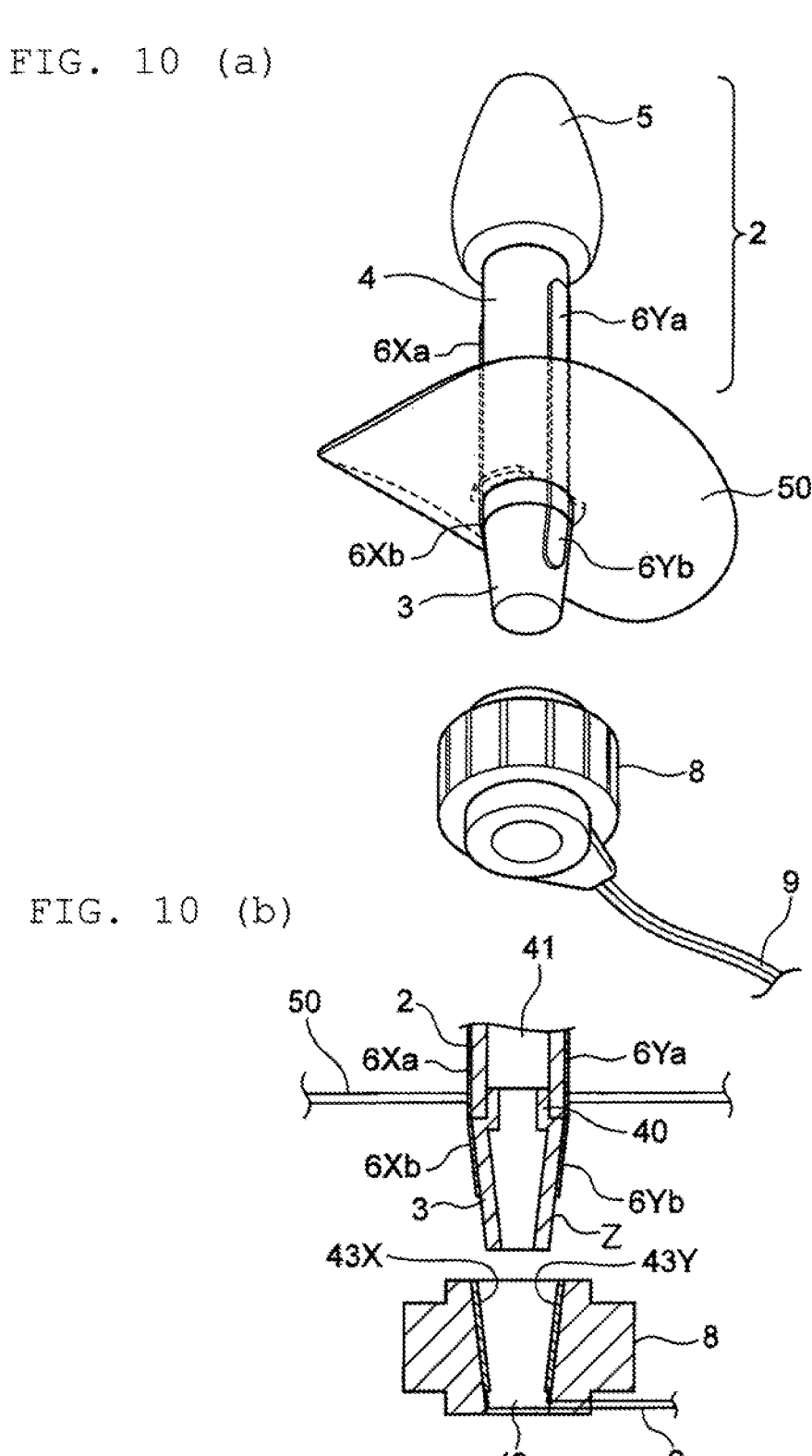
FIG. 10(a) is a perspective view of another example of the probe according to the present invention.
FIG. 10(b) is an explanatory view for illustrating coupling between the insertion portion and the external-device coupler illustrated in FIG. 10(a).

Another example of the probe 1 according to the present invention is illustrated in FIG. 10(a) and FIG. 10(b). The probe 1 is a disassemblable probe in which the insertion portion 2 and the projecting portion 3 can be separated from each other at a suitable position on the base 4 having a rod-like or cylindrical shape in a longitudinal direction of the probe 1. Basic shapes of the insertion portion 2 and the projecting portion 3 are the same as those illustrated in FIG. 1(a). It is preferred that the insertion portion 2 and the projecting portion 3 have a coupling and decoupling structure (coupling and decoupling mechanism) that enables the projecting portion 3 to be separated from the insertion portion 2 by a single operation without the insertion portion 2 being touched by a hand. As an example, the probe 1 illustrated in FIG. 10(b) includes a small-diameter portion 40 at one longitudinal end of the projecting portion 3. The small-diameter portion 40 can be press-fitted into an internal hole 41 of the insertion portion 2 to achieve coupling. When the insertion portion 2 and the projecting portion 3 are coupled to each other, the sensing electrodes 6Xa and 6Ya on the insertion portion 2 and the sensing electrodes 6Xb and 6Yb on the projecting portion 3 become conductive with each other.

The coupler 8 can be fitted over and removed from an outer periphery of the projecting portion 3 of the probe 1 of FIG. 10(a). The coupler 8 of FIG. 10(a) has a ring shape that enables fitting over the outer periphery of the projecting portion 3. As illustrated in FIG. 10(b), the coupler 8 has an internal hole 42 that is tapered downward, and electrodes (coupler electrodes) 43X and 43Y that are formed on an inner surface of the internal hole 42 so as to be opposed to each other.

The coupler 8 can be fitted over and removed from an outer periphery of the projecting portion 3 of the probe 1 of FIG. 10(a). The coupler 8 of FIG. 10(a) has a ring shape that enables fitting over the outer periphery of the projecting portion 3. As illustrated in FIG. 10(b), the coupler 8 has an internal hole 42 that is tapered downward, and electrodes (coupler electrodes) 43X and 43Y that are formed on an inner surface of the internal hole 42 so as to be opposed to each other.

The probe 1 is disposable regardless of whether the probe 1 is an integrated probe or a disassemblable probe. In this case, an inexpensive material suitable for single use, for example, a resin, a rubber, or paper, is used as a material.

[Coupling of External-Device Coupler to Device Mounting Area]

When the internal hole 42 of the coupler 8 of FIG. 10(a) and FIG. 10(b) is fitted over an outer periphery of the device mounting area Z of the probe 1, the coupler 8 is coupled to the projecting portion 3 to make the coupler electrodes 43X and 43Y conductive with the sensing electrodes 6X and 6Y of the probe 1. Thus, the sensing electrodes 6X and 6Y become conductive with the coupler electrodes 43X and 43Y and the signal processing unit 10 via the lead wire 9. As a result, the biosignal detected by the sensing electrodes 6X and 6Y is transmitted to the signal processing unit 10.

In FIG. 10(a) and FIG. 10(b), the sensing electrodes 6X and 6Y of the probe 1 are electrically connected to the external device 7 by coupling the coupler 8 onto the device mounting area Z of the probe 1. However, the coupler 8 may be omitted in some cases. In such a case, the lead wire 9 is directly connected to the sensing electrodes 6X and 6Y of the probe 1, and a distal end of the lead wire 9 is connected to the external device 7. In this case, the projecting portion 3 to which the lead wire 9 is connected may be repeatedly used, and only the insertion portion 2 may be discarded after single use.

(Another Embodiment of Probe)

Figure 11:
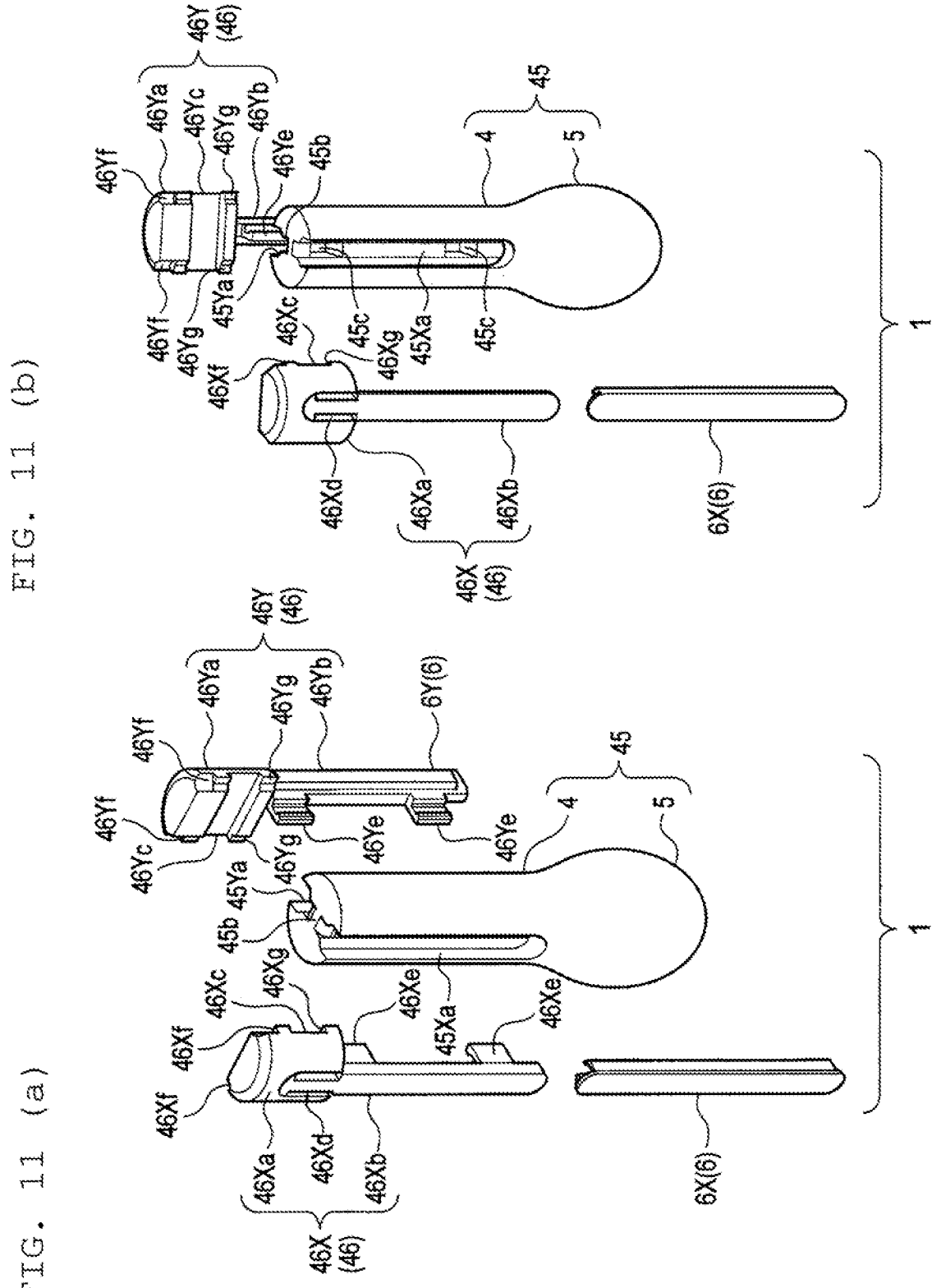
FIG. 11(a) is a perspective view for illustrating an example in which a probe is formed of a plurality of members.
FIG. 11(b) is a perspective view of the probe of FIG. 11(a) when viewed from a different angle.

The integrated probe and the disassemblable probe can each be formed of a plurality of members as illustrated in FIG. 11(a) and FIG. 11(b) in terms of productivity. The probe 1 illustrated in FIG. 11(a) and FIG. 11(b) includes a main body portion 45 and two mounted members 46 (mounted members 46X and 46Y). The main body portion 45 includes the base 4 and the expanded portion 5. The mounted members 46 are mounted onto the main body portion 45.

Two fitting grooves 45Xa and 45Ya, each being longitudinally elongated, are formed in an outer periphery of the base 4 of the main body portion 45 so as to be opposed to each other. Two coupling-portion fitting holes 45c (FIG. 11(b)) are formed in an intermediate portion 45b between the fitting grooves 45Xa and 45Ya so as to be spaced apart from each other in a longitudinal direction of the base 4.

The mounted members 46X and 46Y include head portions 46Xa and 46Ya and shaft-shaped portions 46Xb and 46Yb, respectively. The head portions 46Xa and 46Ya each have a semi-cylindrical shape. The shaft-shaped portions 46Xb and 46Yb are formed to protrude downward from the head portions 46Xa and 46Yz in FIG. 11(a) and FIG. 11(b), respectively. Recessed portions 46Xc and 46Yc, each having a horizontally elongated rectangular shape, are formed on surfaces of the head portions 46Xa and 46Ya, which are opposed to the counterparts of the mounted members 46X and 46Y, respectively. Upper recessed portions 46Xf and 46Yf are formed above the recessed portions 46Xc and 46Yc, and lower recessed portions 46Xg and 46Yg are formed below the recessed portions 46Xc and 46Yc, respectively. Electrode placement portions 46Xd and 46Yd, each extending longitudinally, are formed on arc-shaped surfaces of the head portions 46Xa and 46Ya, respectively.

The shaft-shaped portions 46Xb and 46Yb are rod-shaped portions to be fitted into the fitting grooves 45Xa and 45Ya of the main body portion 45, respectively. The shaft-shaped portions 46Xb and 46Yb include coupling portions 46Xe and 46Ye to be coupled to counterparts of the mounted members 46X and 46Y. The coupling portions 46Xe and 46Ye are formed on surfaces of the shaft-shaped portions 46Xb and 46Yb, which are opposed to the counterparts thereof. Two coupling portions 46Xe and two coupling portions 46Ye are formed on the shaft-shaped portions 46Xb and 46Yb in a protruding manner so as to be spaced apart from each other in a longitudinal direction of the shaft-shaped portions 46Xb and 46Yb, respectively. Each of a distance between the two coupling portions 46Xe and a distance between two coupling portions 46Ye is set to be the same as a distance between coupling-portion fitting holes 45c of the main body portion 45.

In the example illustrated in FIG. 11(a) and FIG. 11(b), the two mounted members 46X and 46Y have the same shape. The same shape of the two mounted members 46X and 46Y allows manufacturing of the mounted members 46X and 46Y with use of a single molding die. Thus, manufacturing cost can be reduced. In the example illustrated in FIG. 11(a) and FIG. 11(b), the coupling portions 46Xe and 46Ye are formed at positions on the right side with respect to a center of the shaft-shaped portions 46Xb and 46Yb in a width direction (lateral direction), respectively. These positions allow connection of opposed inner surfaces of the coupling portions 46Xe and 46Ye when the two mounted members 46X and 46Y are placed to be opposed to each other.

The sensing electrodes 6X and 6Y, each having a U-like shape in sectional view, are fitted over and held onto outer sides of the shaft-shaped portions 46Xb and 46Yb. The sensing electrodes 6X and 6Y are slid from lower ends (ends opposite to the head portions 46Xa and 46Ya) of the shaft-shaped portions 46Xb and 46Yb to cover the outer sides of the shaft-shaped portions 46Xb and 46Yb. When the mounted members 46X and 46Y are mounted onto the main body portion 45, the sensing electrodes 6X and 6Y are exposed to an outside.

Figure 12:
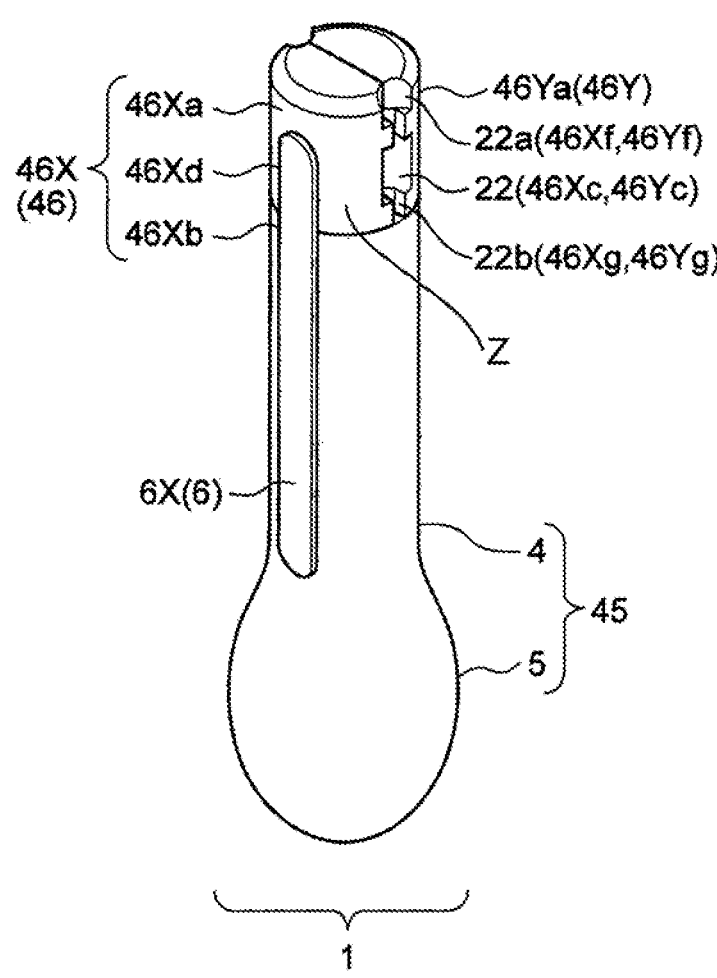

The main body portion 45 and the two mounted members 46X and 46Y are integrated as illustrated in FIG. 12 in the following manner. The shaft-shaped portions 46Xb and 46Yb of the mounted members 46X and 46Y are fitted into the fitting grooves 45Xa and 45Ya of the main body portion 45 to couple the coupling portions 46Xe and 46Ye formed on the shaft-shaped portions 46Xb and 46Yb together in the coupling-portion fitting holes 45c. The upper groove 22 is defined at a position at which the recessed portions 46Xc and 46Yc of the mounted members 46X and 46Y that are coupled together are opposed to each other. An upper fitting groove 22a is defined at a position at which the upper recessed portions 46Xf and 46Yf are opposed to each other, and a lower fitting groove 22b is defined at a position at which the lower recessed portions 46Xg and 46Yg are opposed to each other. The push-in protrusion 36 of the extension arm member 26 is fitted into the upper groove 22. When the rotation stopper portion 32 (see FIG. 5) is formed in a protruding shape, the rotation stopper portion 32 is fitted into the upper fitting groove 22a or the lower fitting groove 22b. The fitting of the rotation stopper portion 32 having a protruding portion into the upper fitting groove 22a or the lower fitting groove 22b prevents spinning of the probe 1.

In the example illustrated in FIG. 11(a) and FIG. 11(b), the sensing electrodes 6X and 6Y, each having a U-like shape in sectional view, are illustrated as an example. For example, the sensing electrodes 6X and 6Y may be formed by attaching electroconductive films, for example, metallic foils onto outer sides of the shaft-shaped portions 46Xb and 46Yb. Further, in the example of FIG. 11(a) and FIG. 11(b), the mounted members 46X and 46Y are coupled together to fix the mounted members 46X and 46Y onto the main body portion 45 as an example. However, the mounted members 46X and 46Y may be individually fixed onto the main body portion 45. Further, in the example illustrated in FIG. 11(a) and FIG. 11(b), the main body portion 45 is formed of one member, and the mounted members 46X and 46Y are formed of two members as an example. However, the main body portion 45 may be formed of two or more members, and each of the mounted members 46 may be formed of one member or formed of three or more members.

[Separation Sheet]

The separation sheet 50 can be mounted onto the base 4 of the probe 1 according to the present invention as illustrated in FIG. 7(a) and FIG. 7(b). The separation sheet 50 illustrated as an example has a disc-like shape, and has a hole 51 formed in a center. The base 4 of the probe 1 can be inserted into the hole 51. The separation sheet 50 may have a shape other than the disc-like shape. It is preferred that the separation sheet 50 be made of an elastic material to allow close contact with the base 4 that has been inserted or be fixed to the base 4 by suitable means, for example, with an adhesive tape or an adhesive so as to prevent positional misalignment in an axial direction of the base 4 or unintended removal from the base 4. The separation sheet 50 is mounted on an outer side of a periphery of the base 4 of the probe 1 to separate a part of the probe 1, which is closer to the insertion portion 2, and a part of the probe 1, which is closer to the coupler 8, from each other. When the insertion portion 2 is inserted into a body organ as illustrated in FIG. 2, the separation sheet 50 can be placed so as to be in contact with buttocks. The separation sheet 50 receives a body fluid (leakage) that leaks from the body organ and flows down the insertion portion 2 to thereby prevent contact of the body fluid with the projecting portion 3 of the probe 1.

The separation sheet 50 is formed separately from the probe 1, and is mountable to and removable from the base 4 of the probe 1. The separation sheet 5 may be mounted in advance onto the base 4, and may be integrated with the base 4 by another means in some cases. It is preferred that the separation sheet 50 be made of an inexpensive disposable material and have water proofness. The separation sheet 50 may also be made of a soft material that can easily be placed so as to be in contact with buttocks or an elastic material that enables easy mounting around the projecting portion 3. The separation sheet 50, which is made of an elastic material, allows easy insertion of the probe 1 into the hole 51 and prevents unintended removal of the probe 1 from the hole 51 after the insertion of the probe 1.

[Packaged Probe]

Figure 9:
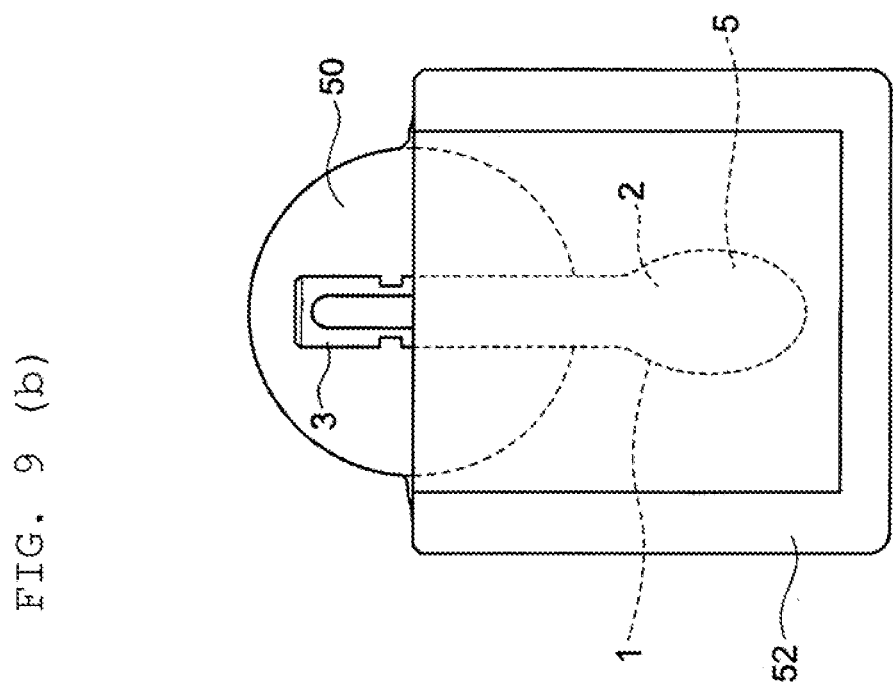
FIG. 9(a) is an explanatory view of a packaged probe according to the present invention.
FIG. 9(b) is an explanatory view for illustrating a state in which an upper half of a package illustrated in FIG. 9(a) is cut away.

The probe 1 and the separation sheet 50 described above can be stored in a package, for example, a packaging bag 52 as illustrated in FIG. 9(a) and FIG. 9(b). The packaging bag 52 illustrated in FIG. 9(a) and FIG. 9(b) is made of a material that allows the packaging bag 52 to be opened with, for example, hands or scissors, and is made of, for example, a resin or paper. When the probe 1 and the separation sheet 50, which are packaged, are used, an upper part of the packaging bag 52 is cut away as illustrated in FIG. 9(b) to allow the separation sheet 50 to be taken out of the packaging bag 52. Then, the projecting portion 3 of the probe 1 that is kept in the packaging bag 52 is directly pushed into the hole 51 of the separation sheet 50 to mount the separation sheet 50 around the probe 1. Next, the coupler 8 (FIG. 5) is mounted onto the device mounting area Z of the probe 1 that is kept (remains) in the packaging bag 52 as illustrated in FIG. 7(a) and FIG. 7(b). In this case, the separation sheet 50 and the coupler 8 can be mounted without allowing the insertion portion 2 of the probe 1 to be touched by a hand. After use, the coupler 8 is removed from the projecting portion 3 of the probe 1. The probe 1, which has been removed from the body organ, is placed into the packaging bag 52 again with the insertion portion 2 side facing downward. The insertion portion 2 is discarded (after single use) together with the packaging bag 52. The package may be other than a packaging bag, and may be a container made of a thin flexible resin or paper. However, it is preferred that the package be made of a material suitable for single use, for example, paper or a resin film, and have a space-saving shape. The probe 1 alone may be packaged.

The packaging bag 52 may be formed to allow the insertion portion 2 side of the probe 1 to be exposed to the outside. In this case, the projecting portion 3 may be held together with the packaging bag 52 with a hand to allow the insertion portion 2 to be inserted into a body organ. In this case, the insertion portion 2 can be inserted into a body organ without being touched by a hand, and thus is hygienic.

[Signal Processing Unit]

The biosignal detected by the sensing electrodes 6X and 6Y is weak regardless of whether the probe 1 is an integrated probe or a disassemblable probe. Thus, it is difficult to directly process the biosignal with an electromyograph. After the biosignal is amplified and an unnecessary signal (mainly, noise) is removed therefrom in the signal processing unit 10, the biosignal is extracted. The signal processing unit 10 measures a potential difference between the thus extracted biosignal and reference electrodes O (FIG. 13) attached onto a different portion of a body surface, for example, a surface of an abdomen.

Figure 13:
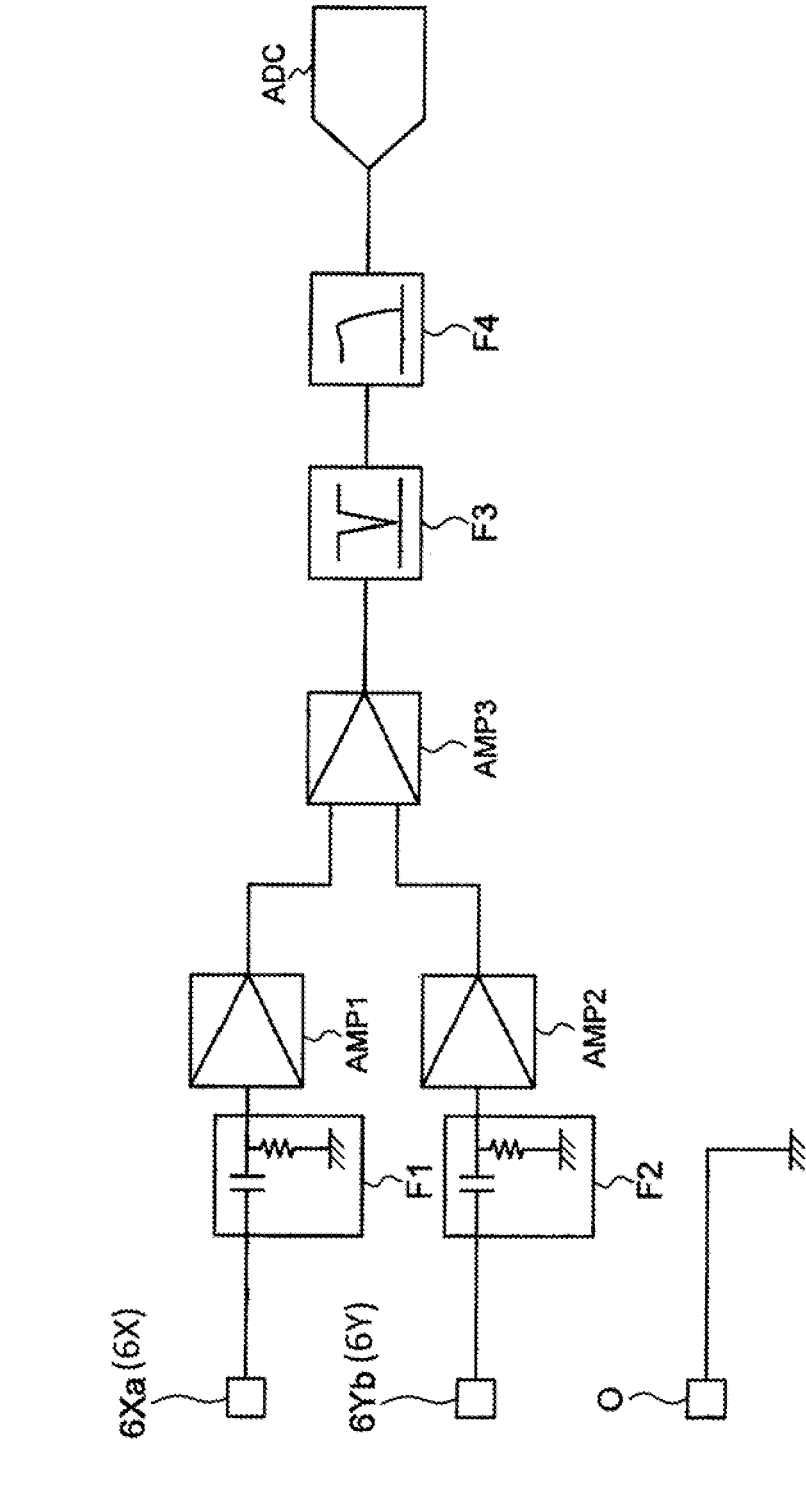
FIG. 13 is an explanatory block diagram of a signal processing unit of an electromyograph.

An example of the external device 7 to be connected to the probe 1 according to the present invention is an electromyograph. An example of the signal processing unit 10 of the electromyograph is illustrated in FIG. 13. The signal processing unit 10 illustrated in FIG. 13 is the same as a signal processing unit of a general-purpose electromyograph. The signal processing unit includes high-pass filters F1 and F2, amplifiers AMP1 and AMP2, a differential amplifier AMP3, a notch filter F3, a low-pass filter F4, and an analog-digital converter ADC. The high-pass filters F1 and F2 are connected to the two sensing electrodes 6X and 6Y of the probe 1, respectively. The amplifiers AMP1 and AMP2 are configured to amplify signals from the high-pass filters F1 and F2, respectively. The notch filter F3 is configured to block passage of a signal at a specific frequency among signals from the differential amplifier and allow passage of a signal at other frequencies. The low-pass filter F4 is configured to allow passage of a low-frequency signal among signals from the notch filter F3.

[Biofeedback Device]

Figure 14:
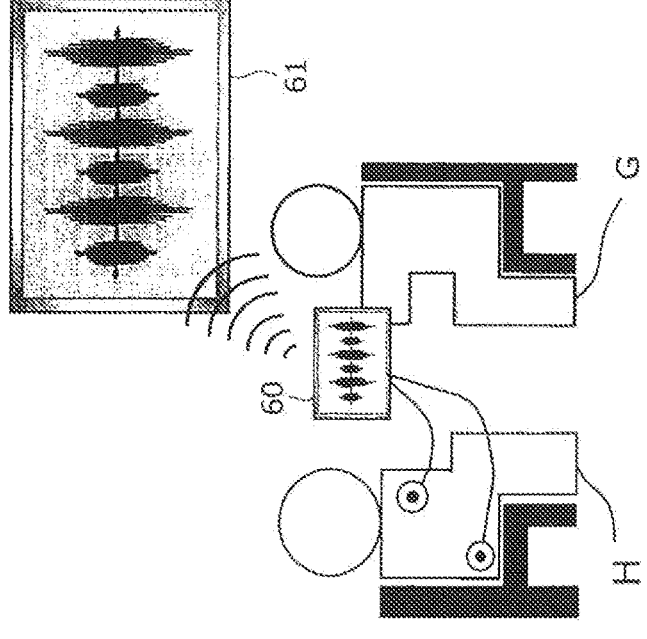
FIG. 14(a) is a schematic view of a biofeedback device according to the present invention.
FIG. 14(b) is an explanatory view for illustrating an evaluation and a treatment using the biofeedback device.
Figure 14:
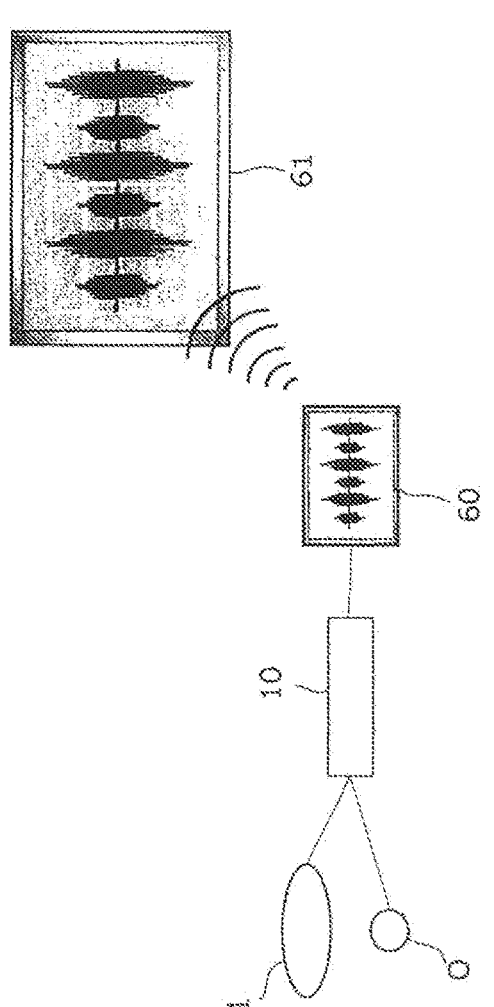
Figure 15:
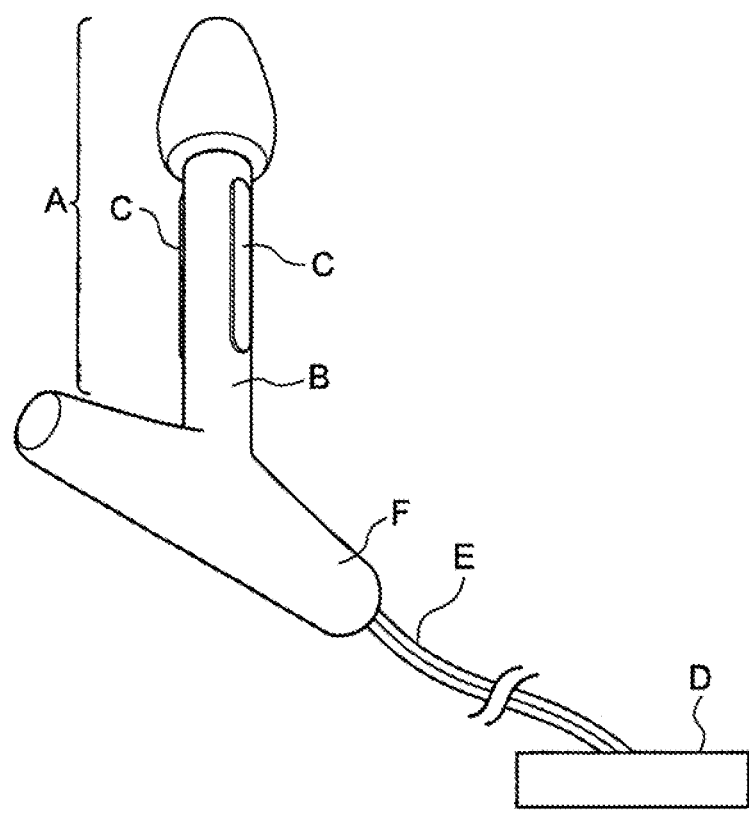
FIG. 15 is an explanatory view of a related-art probe.

A biofeedback device according to the present invention includes a monitor 60. As illustrated in FIG. 14(a), the sensing electrodes 6 of the probe 1 and the reference electrodes (electromyograph electrodes) O attached at suitable positions on a body surface are connected to the signal processing unit 10. The signal processing unit 10 is connected to the monitor 60. An image generated based on the biosignal that has been processed in the signal processing unit 10 is displayed on the monitor 60. The same image signal as the image signal is transmitted wirelessly or in a wired manner to a large auxiliary monitor 61 to display an image thereon. The image can be checked (viewed) by a doctor H and a patient H as illustrated in FIG. 14(*b*) to be used for biofeedback evaluations and treatments. The signal processing unit 10 can also generate perceivable information other than image information, for example, audio information based on the biosignal. The perceivable information described above can be stored in a storage device.

INDUSTRIAL APPLICABILITY

The embodiments described above are each an example of the present invention, and the present invention is not limited to the embodiments described above. In the case of the disassemblable probe, in particular, for example, the coupling and decoupling structure for the insertion portion 2 and the projecting portion 3, the structure (mechanism) and the shape of the coupler 8 configured to allow connection between the projecting portion 3 of the probe 1 and the signal processing unit 10, a coupling structure for the projecting portion 3 and the coupler 8 may be other configurations (mechanisms) as long as the object of the present invention is achieved. Further, the probe 1 illustrated in the drawings may also be inserted into measurement sites other than an anus or a vagina, for example, a urethra or other sites to which the probe 1 can be inserted, and can be used to detect a biosignal of a muscle other than pelvic floor muscles. In this case, the probe 1 is designed to have a shape, a size, and other dimensions that allow easy insertion into the measurement site and prevent unintended removal therefrom. The probe 1 may be used not only to detect the biosignal but also to electrically stimulate various kinds of muscles of body organs. In this case, a device capable of generating a stimulus signal is used as the external device.

REFERENCE SIGNS LIST

1 probe
2 insertion portion
3 projecting portion
4 base
5 expanded portion
6, 6X, 6Y sensing electrode
6Xa, 6Ya sensing electrode (of insertion portion)
6Xb, 6Yb sensing electrode (of projecting portion)
7 external device (electromyograph)
8 external-device coupler (coupler)
9 lead wire
10 signal processing unit
11 male coupler member
12 female coupler member
13 (13X, 13Y) male electrode
14 (14X, 14Y) insertion hole
15 protrusion
16 recessed portion
17 (17X, 17Y) clamping electrode
18 (18X, 18Y) operating portion
20 (20X, 20Y) electrode protrusion
21 division groove
22 upper groove
22a upper fitting groove
22b lower fitting groove

23 lower groove
24 rotation stopping protrusion
25 coupler main body
26 extension arm member
27 fitting hole
27a regulating protrusion
28 fitting recessed portion
29 fitting plate
30 retaining protrusion
31 (31X, 31Y) electrode protrusion (coupling electrode)
32 rotation stopper portion
33 upper plate
34 lower plate
35 fitting groove
36 push-in protrusion
37 stopper
40 small-diameter portion
41 internal hole (of insertion portion)
42 internal hole (of coupler)
43X, 43Y electrode (coupler electrode)
45 main body portion
45Xa, 45Ya fitting groove
45b intermediate portion
45c coupling-portion fitting hole
46 (46X, 46Y) mounted member
46Xa, 46Ya head portion
46Xb, 46Yb shaft-shaped portion
46Xc, 46Yc recessed portion
46Xd, 46Yd electrode placement portion
46Xe, 46Ye coupling portion
46Xf, 46Yf upper recessed portion
46Xg, 46Yg lower recessed portion
50 separation sheet
51 hole (of separation sheet)
52 packaging bag
60 monitor
61 auxiliary monitor
A insertion portion
B shaft
C electrode
D signal processing unit
E lead wire (cable)
F handle
G doctor
H patient
O reference electrode
Z device mounting area
ADC analog-digital converter
AMP1, AMP2 amplifier
AMP3 differential amplifier
F1, F2 high-pass filter
F3 notch filter
F4 low-pass filter

The invention claimed is:

1. An electromyograph probe comprising:

a probe to be inserted into a body organ to obtain a biosignal; and an external-device coupler removably mounted on the probe;

wherein the probe includes:

an insertion portion insertable into the body organ, a projecting portion that is exposed to an outside of a body after the insertion portion is inserted into the body organ, sensing electrodes that detect the biosignal when the insertion portion is inserted into the body organ, and a device mounting area onto which the external-device coupler is removably mounted, wherein the insertion portion and the projecting portion are integrally formed, wherein an end of the projecting portion is divided into two parts by a division groove, wherein the projecting portion comprises a first groove and a second groove in a peripheral surface thereof, wherein the sensing electrodes are provided at least on an outer peripheral surface of the insertion portion, wherein the external-device coupler includes a coupler main body and an extension arm member, wherein the coupler main body includes a fitting hole in which the probe is fitted, a fitting recessed portion that is communicating with the fitting hole and opened to outer periphery of the coupler main body, and coupling electrodes that become electrically conductive with the sensing electrodes, wherein the extension arm member includes a push-in protrusion configured to be inserted into the first groove, a plate configured to be received by the second groove when the push-in protrusion is inserted into the first groove, wherein said two parts of the projecting portion are forced apart from each other and electrode protrusions of the sensing electrodes contact electrode protrusions of the coupling electrodes so that the sensing electrodes become electrically conductive with the coupling electrodes, when the extension arm member is pushed into the fitting recessed portion and the push-in protrusion is inserted into the first groove in a state in which the external-device coupler is mounted onto the probe so that the device mounting area of the probe fits into the fitting hole of the coupler main body.

2. The electromyograph probe according to claim 1, wherein the whole probe is disposable.

3. A biofeedback device for perceptualizing a biosignal, the biofeedback device comprising:

the electromyograph probe of claim 2;

a biosignal processing unit configured to process the biosignal obtained by the sensing electrodes of the electromyograph probe into perceivable information; and a display unit configured to visibly display the processed perceivable information processed by the biosignal processing unit.

4. The electromyograph probe according to claim 1, wherein a separation sheet is mounted on the probe.

5. The electromyograph probe according to claim 4, wherein the separation sheet is disposable.

6. A biofeedback device for perceptualizing a biosignal, the biofeedback device comprising:

the electromyograph probe of claim 5;

a biosignal processing unit configured to process the biosignal obtained by the sensing electrodes of the electromyograph probe into perceivable information; and a display unit configured to visibly display the processed perceivable information processed by the biosignal processing unit.

7. A biofeedback device for perceptualizing a biosignal, the biofeedback device comprising:

the electromyograph probe of claim 4;

a biosignal processing unit configured to process the biosignal obtained by the sensing electrodes of the electromyograph probe into perceivable information; and a display unit configured to visibly display the processed perceivable information processed by the biosignal processing unit.

8. The electromyograph probe according to claim 1, further comprising:

a package configured to contain the probe, wherein the package has a shape and a size that enable individual packaging of the probe, and wherein the shape and the size of the package are such that, when a part of the package is cut away to open the package, the insertion portion or the projecting portion of the probe is exposed to an outside of the package and another one of the insertion portion and the projecting portion of the probe is contained in a remaining part of the package.

9. A biofeedback device for perceptualizing a biosignal, the biofeedback device comprising:

the electromyograph probe of claim 8;

a biosignal processing unit configured to process the biosignal obtained by the sensing electrodes of the electromyograph probe into perceivable information; and a display unit configured to visibly display the processed perceivable information processed by the biosignal processing unit.

10. A biofeedback device for perceptualizing a biosignal, the biofeedback device comprising:

the electromyograph probe of claim 1;

a biosignal processing unit configured to process the biosignal obtained by the sensing electrodes of the electromyograph probe into perceivable information; and a display unit configured to visibly display the processed perceivable information processed by the biosignal processing unit.

11. The electromyograph probe according to claim 1, wherein a regulating protrusion is formed on an inner peripheral surface of the fitting hole of the coupler main body in order to prevent upside-down insertion of the probe.

12. A biofeedback device for perceptualizing a biosignal, the biofeedback device comprising:

the electromyograph probe of claim 11;

a biosignal processing unit configured to process the biosignal obtained by the sensing electrodes of the electromyograph probe into perceivable information; and a display unit configured to visibly display the processed perceivable information processed by the biosignal processing unit.

* * * * *